(12) United States Patent
Kim et al.

(10) Patent No.: US 8,343,940 B2
(45) Date of Patent: Jan. 1, 2013

(54) METHOD FOR ENHANCING CHEMICAL SENSITIVITY OR RADIOSENSITIVITY OF CANCER CELLS BY INHIBITING EXPRESSION OF TSPYL5

(75) Inventors: In Gyu Kim, Daejeon (KR); Tae Lim Kim, Daejoen (KR); Kug Chan Kim, Daejeon (KR); Eun Jin Kim, Daejeon (KR); So Yong Lee, Cheongju-si (KR); Il Lae Jung, Daejeon (KR)

(73) Assignee: Korea Atomic Energy Research Institute (KR)

( * ) Notice: Subject to any disclaimer, the term of this patent is extended or adjusted under 35 U.S.C. 154(b) by 76 days.

(21) Appl. No.: 12/823,035

(22) Filed: Jun. 24, 2010

(65) Prior Publication Data

US 2011/0111400 A1    May 12, 2011

(30) Foreign Application Priority Data

Nov. 12, 2009 (KR) .......................... 10-2009-0109125

(51) Int. Cl.
*C12N 15/11* (2006.01)
*C07H 21/02* (2006.01)
*C07H 21/04* (2006.01)
(52) U.S. Cl. ..................................... 514/44 A; 536/24.5
(58) Field of Classification Search ........................ None
See application file for complete search history.

(56) References Cited

OTHER PUBLICATIONS

Kim et al (Cancer Res 2006; 66: (15). Aug. 1, 2006).*
Murray et al (J. Biol. Chem. 268(21): 15847-15853, 1993.*
Heng et al (J. Cell. Physiol. 220: 538-547, 2009).*
Jung, Yeonjoo et al. (2008), "Gene silencing of TSPYL5 mediated by aberrant promoter methylation in gastric cancers," Laboratory Investigation, vol. 88 Feb. 2008, pp. 153-160.
Kim, Eun Jin et al. (2010), "TSPYL5 is involved in cell growth and the resistance to radiation in A549 cells via the regulation of p21$^{WAF1/Cip1}$ and PTEN/AKT pathway," Biochemical and Biophysical Research Communications 392 (2010) 448-453.
Kim, Tae-You et al. (2006), "Epigenomic Profiling Reveals Novel and Frequent Targets of Aberrant DNA Methylation-Mediated Silencing in Malignant Glioma," Cancer Res 2006,66(15):7490-7501.
Vachani, Anil et al. (2007), "A 10-Gene Classifier for Distinguishing Head and Neck Squamous Cell Carcinoma and Lung Squamous Cell Carcinoma," Clin Cancer Res 2007; 13(10):2905-2915.

* cited by examiner

*Primary Examiner* — Richard Schnizer
(74) *Attorney, Agent, or Firm* — Greenlee Sullivan P.C.

(57) ABSTRACT

Disclosed herein is a method for enhancing sensitivity of cancer cells to compounds or radiation by inhibiting the expression of testis-specific protein, Y-encoded like 5 (TSPYL5). More specifically, because methylation of TSPYL5 protein expressed in lung cancer cell line was inhibited to increase the expression level of the gene, resistance to stress such as radiation or anticancer agents was increased. Because the sensitivity of cancer cells to stress such as radiation or anticancer agents was increased by inhibiting the expression of the TSPYL5 gene to promote the apoptosis of the cells, an anticancer supplement agent containing an inhibitor of the expression or activity of the TSPYL5 gene of the present invention inhibits the growth of cancer cells and enhances the sensitivity to various stresses to maximize the apoptosis. Thus, when used in combination with radiotherapy or chemotherapy, the anticancer supplement agent may be used very usefully for anticancer treatment.

1 Claim, 8 Drawing Sheets

METHOD FOR ENHANCING CHEMICAL SENSITIVITY OR RADIOSENSITIVITY OF CANCER CELLS BY INHIBITING EXPRESSION OF TSPYL5

CROSS-REFERENCES TO RELATED APPLICATION

This patent application claims the benefit of priority from Korean Patent Application. No. 10-2009-0109125, filed on Nov. 12, 2009, the contents of which are incorporated herein by reference.

BACKGROUND OF THE INVENTION

1. Field of the Invention

The present disclosure relates to a method for enhancing the chemical sensitivity or radiosensitivity of cancer cells by inhibiting the expression of testis-specific protein, Y-encoded-like 5 (TSPYL5).

2. Description of the Related Art

DNA methylation is one of chemical modifications that controls the expression of genetic traits, inhibits the expression of genes by reducing the reactivity of DNA and increasing the stability of DNA, and is essential for normal development. DNA methylation occurs mainly on the cytosine of CpG islands in the promoter region of a specific gene to interfere with the binding of transcription factors, thus silencing the expression of the gene. In particular, the expression of a specific gene modified by DNA hypermethylation is deeply associated with human diseases such as cancer or tumor. Thus, the promoter methylation of tumor-associated genes is an important indication of cancer, and may be used in many applications, including the diagnosis and early diagnosis of cancer, the prediction of cancer development, the prediction of prognosis of cancer, follow-up examination after treatment, and the prediction of responses to anticancer therapy.

The onset of cancer occurs through a sequence of genetic mutations. It has been found that although these genetic mutations may be accompanied by genetic changes in a DNA base sequence, epigenetic changes, which inhibit the expression of genes without being accompanied by the genetic changes in a DNA base sequence, are also important, and it has been noted that these genetic mutations are involved in the expression of various tumor-associated genes during the onset of cancer. Epigenetic changes such as promoter CpG island hypermethylation and histone modification are important mechanisms for carcinogenesis. About 60-70% of human genes have CpG islands in the promoter and some of these genes are hypermethylated to block the expression of the corresponding cancer-related gene, thus affecting tumor onset.

It has been reported that the expression of 160 or more genes is increased in the glioma cell line by inhibitors of DNA methylation and histone deacetylation. And then the TSPYL5 gene, encoding testis-specific protein, Y-encoded-like 5, is one of them, and it has been shown that the expression of the gene is significantly induced. It has been reported that the TSPYL5 gene is DNA methylated at a high frequency in a glial tumor and glioma cell line, and silenced with the CST6 gene, a metastasis suppressor and the BIK gene, an apoptosis-inducer (Kim. T. Y. et al., Cancer Res. 66(15):7490-7501, 2006). It was also confirmed that the expression of the TSPYL5 gene was often reduced in gastric cancer cell lines, 7 of 9 gastric cancer cell lines were deactivated by DNA methylation, the expression level of TSPYL5 was very low, and the promoter of the TSPYL5 gene was hypermethylated in 23 of the 36 primary gastric tumor cases. It has been also reported that the TSPYL5 gene is one of the 10 plausible genes with which Head and Neck Squamous Cell Carcinoma may be differentiated from Lung Squamous Cell Carcinoma (Anil Vachani. et al., Cancer Res. 13(10):2905-2915, 2007). However, the cellular physiological functions of the TSPYL5 gene still have not been well known.

Thus, the present inventors have performed research to understand the effects of the TSPYL5 gene on anticancer agent sensitivity and radiosensitivity, examined the expression of the TSPYL5 gene by using lung cancer cell lines, and confirmed that the expression of TSPYL5 was reduced in the H460 cell line, a cell line sensitive to radiation and anticancer agents, by DNA hypermethylation in the promoter region of the TSPYL5 gene. When the present inventors used siRNA to inhibit the expression of the TSPYL5 protein in a lung cancer cell line (A549 or H1299) based on a confirmed result that the degree of methylation was reduced in an A549 or H1299 cell line, a cell line highly resistant to radiation and anticancer agents, it was confirmed that the sensitivity to anticancer agents and radiation was significantly increased. When siRNA was used to inhibit the expression of the TSPYL5 protein in lung cancer cell line (A549 or H1299), the sensitivity to anticancer agents and radiation was significantly increased. Thus, the present inventors revealed that the use of inhibitors of expression or activity of TSPYL5 in combination with radiotherapy or chemotherapy may contribute to anticancer treatment very effectively, and made the present invention.

SUMMARY OF THE INVENTION

One object of the present invention is to provide a method for enhancing apoptotic effects of cancer cells by inhibiting the expression of testis-specific protein, Y-encoded-like 5 (TSPYL5) gene to enhance sensitivity of the cancer cells to compounds or radiation.

In order to achieve the object, the present invention provides a method for enhancing sensitivity of cancer cells to compounds or radiation, including: administering to the cancer cells an anticancer supplement agent containing an inhibitor of the expression or activity of testis protein, Y-encoded-like 5 (TSPYL5) protein having an amino acid sequence represented by SEQ ID No: 1.

The present invention also provides a method for screening a material for enhancing sensitivity of cancer cells to compounds or radiation, including:

1) treating a TSPYL5 protein expression cell line with a subject material;

2) measuring a degree of methylation of a TSPYL5 gene in the cell line; and 3) selecting a subject material with an enhanced degree of methylation in the TSPYL5 gene compared to a control group which has not been subjected to a treatment of the subject material.

Furthermore, the present invention provides a method for screening a material for enhancing sensitivity of cancer cells to compounds or radiation, including:

1) treating a TSPYL5 protein expression cell line with a subject material;

2) measuring a degree of expression or activity of a TSPYL5 protein in the cell line; and 3) selecting a subject material with an decreased degree of expression or activity of the TSPYL5 gene compared to a control group which has not been subjected to a treatment of the subject material.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical spirit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a method for enhancing sensitivity of cancer cells to compounds or radiation, including administering to the cancer cells an anticancer supplement agent containing an inhibitor of the expression or activity of the testis protein, Y-encoded-like 5 (TSPYL5) protein.

The TSPYL5 protein preferably has an amino acid sequence represented by SEQ ID No: 1, but is not limited thereto.

The anticancer supplement agent preferably enhances the sensitivity of cancer cells to compounds or radiation, but is not limited thereto.

The cancer cell may be preferably, but is not limited to, lung cancer cell, and include all cancer cells in which TSPYL5 protein is overexpressed.

The compounds preferably include one selected from the group consisting of, but not limited to, cisplatin, methyl methane-sulfonate (MMS), and hydrogen peroxide ($H_2O_2$).

The radiation may be gamma-radiation, x-ray or electron ray, more preferably gamma-radiation, but is not limited thereto.

The inhibitor of the expression of the TSPYL5 protein preferably includes an antisense nucleotide or small interfering RNA (siRNA) complementarily binding to mRNA of a TSPYL gene, and the inhibitor of the activity of the TSPYL5 protein preferably includes one selected from the group consisting of, but not limited to, compound complementarily binding to TSPYL5 protein, peptide, peptide mimetics, and antibody.

The siRNA consists of a sense sequence of 15 to 30mers selected in the base sequence of mRNA of a gene (SEQ ID No: 2) encoding a human TSPYL5 protein and an antisense sequence complementarily binding to the sense sequence. Then, the sense sequence preferably consists of, but not specifically limited to, 25 bases, more preferably has a base sequence represented by SEQ ID Nos.: 8, 9, 10, 11, 12, or 13, and most preferably has a base sequence represented by SEQ ID Nos.: 10 or 11.

The antisense nucleotide, as defined in the Watson-Crick base pair, binds to a complementary base sequence of DNA, immature-mRNA, or mature mRNA (hybridization) to interfere with the flow of genetic information as a protein in the DNA. The properties of antisense nucleotides specific to a target sequence allow them to be exceptionally multifunctional. Because the antisense nucleotide is a long chain of monomer units, they may be easily synthesized by a target RNA sequence. Recently, numerous studies have demonstrated that the antisense nucleotide is available as a biochemical means to study a target. Due to recent progresses in the fields of oligonucleotide chemistry and nucleotide synthesis exhibiting enhanced cell adsorption, affinity for binding to a target, and nuclease resistance, the use of antisense nuclease may be considered as a new type of inhibitor.

The peptide mimetics are peptides or non-peptides which inhibit the binding domain of the TSPYL5 protein and inhibit the activity of the TSPYL5 protein. The major residues of a non-hydrolyzable peptide analogue are prepared by using β-turn dipeptide core, keto-methylene pseudopeptides, azepine, benzodiazepine, β-aminoalcohol, and substituted gamma-lactam ring.

In order to confirm the expression level of the TSPYL5 protein in accordance with sensitivity to anticancer agents and radiation in a lung cancer cell line, the present inventors compared the expression levels of the TSPYL5 gene in A549, H460, and H1299 cell lines through microarray and reverse transcription polymerase chain reaction (RT-PCR). The results show that the expression levels of TSPYL5 in A549 and H1299 cell lines with resistance to anticancer agents and radiation were significantly increased compared to H460 cell line with sensitivity to anticancer agents and radiation (See FIGS. 1 & 2). Thus, it can be understood that the overexpression of the TSPYL5 enhances the resistance to anticancer agents and radiation.

In order to confirm the methylation status of the TSPYL5 gene in a lung cancer cell line in accordance with the expression level of TSPYL5, the present inventors performed pyrosequencing on the promoter of the TSPYL5 gene in A549, H460, and H1299 cell lines. The results show that the methylation was increased in the H460 cell more than in the A549 and H1299 cells (See FIG. 3). Thus, it can be understood that the expression level of the TSPYL5 gene was increased due to reduced methylation in the A549 and H1299 cells while that of the TSPYL5 gene was significantly decreased in the H460 cell due to hypermethylation.

Figure 4:
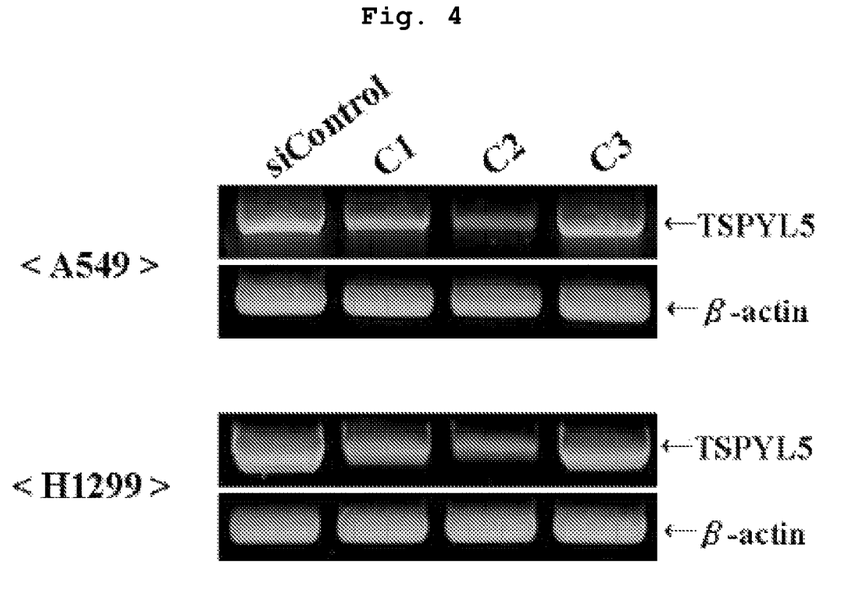
FIG. 4 is a group of photos illustrating the expression of TSPYL5 in a cell transduced with Scrambled Stealth™ RNA molecule (negative control; siControl) and cells each transduced with 3 kinds of TSPYL5-siRNA duplex oligoribonucleotide candidate primers (C1-131713, C2-131714, and C3-131715) in A549 and H1299 cells.

In order to confirm the effects of inhibition of the expression of TSPYL5 on sensitivity of cells to anticancer agents and radiation, the present inventors confirmed that the expression of the gene was inhibited by transduction of siRNA of the TSPYL5 gene and the expression level of the TSPYL5 gene was inhibited by transduction of siRNA through RT-PCR (See FIG. 4). Through flowcytometry, the sensitivity of cells to anticancer agents was also identified by using cisplatin, and the sensitivity of cells to gamma-radiation was identified by flowcytometry and colony formation assay. The results show that the sensitivity of cells to anticancer agents and radiation was increased in a lung cancer cell in which the TSPYL5 gene had been inhibited (See FIGS. 5, 6, and 7). Thus, it can be understood that the expression level of the TSPYL5 gene affects the sensitivity of cells to anticancer agents and radiation. It was also confirmed that the TSPYL5 gene regulates factors associated with growth inhibition of cells, apoptosis, and resistance (See FIG. 8).

Therefore, when DNA damaging agents such as anticancer agents or radiation are used in treatment of cancer cells to inhibit the expression or activity of a gene encoding the TSPYL5 protein, it can be understood that apoptosis is enhanced, and the sensitivity of cancer cells to anticancer agents or radiation may be enhanced by administering an inhibitor of the expression or activity of a gene encoding the TSPYL5 protein.

An anticancer supplement agent containing an inhibitor of the expression or activity of the TSPYL5 protein of the present invention as an active ingredient may include about 0.0001 to about 50 wt % of the active ingredient based on the total weight.

The anticancer agent of the present invention may contain at least one active ingredient exhibiting identical or similar functions in addition to the inhibitor of the expression or activity of the TSPYL5 protein.

The anticancer agent of the present invention may be prepared by including at least one pharmaceutically acceptable carrier in addition to the active ingredient described above for administration. For the pharmaceutically acceptable carriers, saline, sterilized water, Ringer's solution, buffered saline, dextrose solution, maltodextrin solution, glycerol, ethanol, liposome and a mixture of one or more thereof can be used. If necessary, a general additive such as an antioxidant, buffer and an antimicrobial agent may be additionally added. Diluents, dispersants, surfactants, binders and lubricants may be additionally added for injection formulations such as aqueous solution, suspension and emulsion, and formulations into pills, capsules, granules or tablets. The carrier may be used in the form of being coupled to a target-specific antibody or other ligands in order for the effective ingredient to act in a target-specific manner. Furthermore, the composition may be preferably formulated depending on its diseases or components, using a suitable method known in the art.

The nucleotide or nucleic acid used in the present invention may be formulated for oral, topical, parenteral, intranasal, intravenous, intramuscular, subcutaneous, intraocular and transdermal administration. Preferably, the nucleic acid or vector is used in an injectable form. Accordingly, an injectable anticancer supplement agent may be mixed with any pharmaceutically acceptable vehicle, especially for a direct injection at the level of the site to be treated. This may be, in particular, sterile or isotonic solutions, or dry, especially freeze-dried, compositions which, upon addition, depending on the case, of sterilized water or of physiological saline, allow the preparation of injectable solutions. A direct injection of nucleic acid into the patient's tumor is advantageous because it makes it possible to concentrate the therapeutic effect at the level of the affected tissues. It is advantageous that the direct injection of nucleic acid into the tumor of a patient allows the treatment to be focused on an affected tissue. The dosages of nucleic acid used may be adjusted according to various parameters, and especially according to the gene, vector, mode of administration used, disease in question or alternatively the desired duration of treatment. The dosages may vary according to patient's weight, age, sex, health condition, diet, administration time, administration method, excretion rate, severity of disease, etc. Daily dosage is about 0.001 mg/kg to 100 mg/kg, and preferably, 0.01 mg/kg to 10 mg/kg. It is desirable to administer the composition once or dividedly several times per day.

The present invention also provides a method for screening a material for enhancing the sensitivity of cancer cells to compounds or radiation, including:
1) treating a TSPYL5 protein expression cell line with a subject material;
2) measuring a degree of methylation of the TSPYL5 gene in the cell line; and
3) selecting a subject material with an enhanced degree of methylation in the TSPYL5 gene compared to a control group which has not been subjected to a treatment of the subject material.

In the method, the TSPYL5 protein in Step 1) preferably has an amino acid sequence represented by SEQ ID No: 1, but is not limited thereto.

In the method, the measuring of a degree of methylation in Step 2) is preferably performed by one selected from the group consisting of, but not limited to, polymerase chain reaction (PCR), methylation specific PCR, real time methylation specific PCR, PCR using methylated DNA-specific binding protein, quantitative PCR, DNA chip, pyrosequencing, and bisulfite sequencing, and all the methods for measuring an amount of transcripts or proteins coded therefrom known to those skilled in the art may be used.

In the method, the compound preferably includes one selected from the group consisting of cisplatin, methyl methane-sulfonate (MMS), and hydrogen peroxide ($H_2O_2$), the radiation includes gamma-radiation, x-ray, or electron ray, most preferably, gamma-radiation, but are not limited thereto.

In the method, the cancer cell preferably is a lung cancer cell, is not limited thereto, and may include all the cancer cells in which the TSPYL5 protein is overexpressed.

In the present invention, it was confirmed that the TSPYL5 gene regulated the expression level through methylation associated with resistance to stress. A significant increase in resistance to anticancer agents and gamma-radiation was observed when the TSPYL5 protein was overexpressed in a lung cancer cell line while a significant increase in sensitivity to anticancer agents and radiation was confirmed when the expression of the TSPYL5 protein was inhibited by using siRNA.

Therefore, a material that may enhance the sensitivity of cancer cells to compounds or radiation may be screened by selecting a subject material by which methylation of the TSPYL5 gene is increased.

Furthermore, the present invention provides a method for screening a material for enhancing the sensitivity of cancer cells to compounds or radiation, including:

1) treating a TSPYL5 protein expression cell line with a subject material;

2) measuring a degree of expression or activity of the TSPYL5 protein in the cell line; and 3) selecting a subject material with an decreased degree of expression or activity of the TSPYL5 gene compared to a control group which has not been subjected to a treatment of the subject material.

In the method, the TSPYL5 protein in Step 1) preferably has an amino acid sequence represented by SEQ ID No: 1, but is not limited thereto.

In the method, the degree of expression of the protein in Step 2) is preferably measured by one selected from the group consisting of, but not limited to, immunoprecipitation, radioimmunoassay (RIA), Enzyme-Linked Immunosorbent Assay (ELISA), immunohistochemistry, RT-PCR, Western Blotting, and flowcytometry (FACS), and all the methods for measuring an amount of transcripts or proteins coded therefrom known to those skilled in the art may be used. The degree of activity of the protein is preferably measured by one selected from the group consisting of, but not limited to, SDS-PAGE, immunofluorescence, Enzyme-Linked Immunosorbent Assay (ELISA), mass spectrometry, and protein chip.

In the method, the cancer cell preferably is a lung cancer cell, is not limited thereto, and may include all the cancer cells in which the TSPYL5 protein is overexpressed.

In the method, the compound preferably includes one selected from the group consisting of cisplatin, methyl methane-sulfonate (MMS), and hydrogen peroxide ($H_2O_2$), the radiation includes gamma-radiation, x-ray, or electron ray, most preferably, gamma-radiation, but are not limited thereto.

In the present invention, it was confirmed that the TSPYL5 gene regulated the expression level through methylation associated with resistance to stress. A significant increase in resistance to anticancer agents and gamma-radiation was observed when the TSPYL5 protein was overexpressed in a lung cancer cell line while a significant increase in sensitivity to anticancer agents and radiation was confirmed when the expression of the TSPYL5 protein was inhibited by using siRNA.

Therefore, a material that may enhance the sensitivity of cancer cells to compounds or radiation may be screened by selecting a subject material by which a degree of expression or activity of the TSPYL5 protein is decreased.

Hereinafter, the present invention will be described in more detail with reference to the following examples. However, the following examples are provided for illustrative purposes only, and the scope of the present invention should not be limited thereto in any manner.

Example 1

Confirmation of Expression Level of the TSPYL5 Gene in Lung Cancer Cell

<1-1> Confirmation of Expression Level of the TSPYL5 Gene in a Lung Cancer Cell Line by Microarray In order to compare the expression levels of TSPYL5 in lung cancer cell lines A549, H460, and H1299 obtained from Korean Cell Line Bank, Cancer Research Center and Cancer Research Institute, Seoul National University of Medicine, microarray was performed by a method well known to those skilled in the art.

Figure 1:
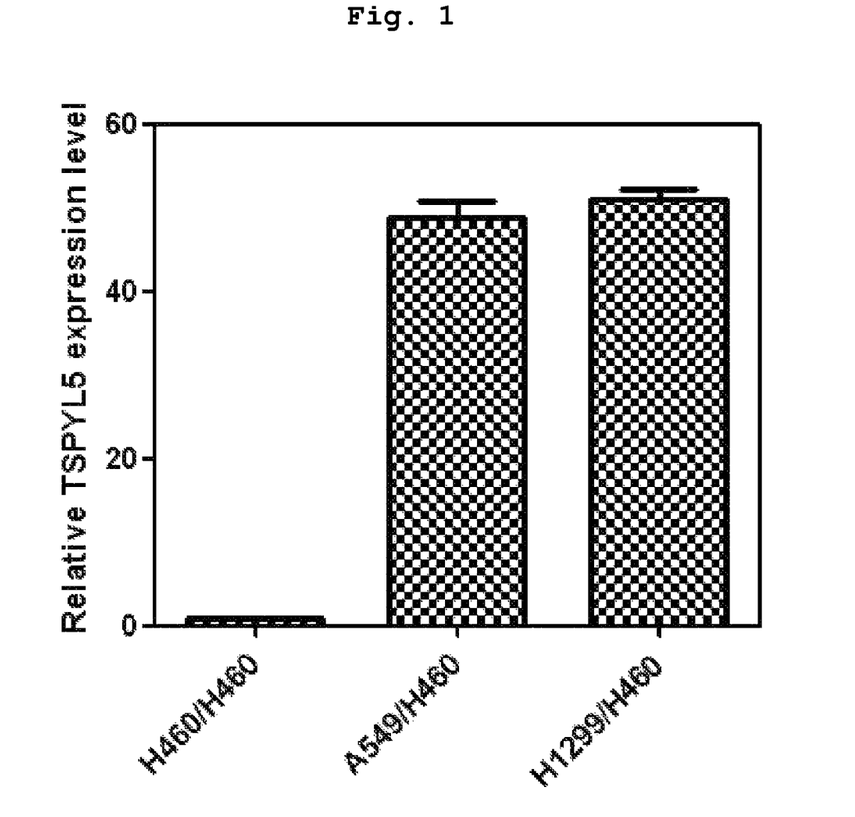
FIG. 1 is a graph illustrating a measurement of the expression level of TSPYL5 in lung cancer cell lines A549, H460, and H1299 by using a microarray.

As illustrated in FIG. 1, the results show that the expression levels of TSPYL5 in the A549 and H1299 cell lines with resistance to anticancer agents and radiation were increased more than that in the non small cell lung cancer cell line H460 with sensitivity to anticancer agents and radiation by about 50 times (FIG. 1).

<1-2> Confirmation of Expression Level of TSPYL5 in Lung Cancer Cell Line Through Reverse Transcription Polymerase Chain Reaction (RT-PCR)

In order to compare the expression levels of TSPYL5 in lung cancer cell lines A549, H460, and H1299, reverse transcription polymerase chain reaction (RT-PCR) was performed. The RT-PCR was performed in the following manner: a mixture of 10 mM dNTPs, 5×RT buffer, 0.5 μg/μl oligo dT, addition of each of 4 μg of heat denaturated (70° C., 10 min) total RNA of lung cancer cell lines H460, A549, and H1299, and 200 U/μl M-MLV RTase, 0.02% diethyl pyrocarbonate (DEPC)-treated sterilized water to a final volume of 20 μl, followed by reaction at 45° C. for 30 min. Next, the mixture was heated to 94° C. for 5 min, and then snap-cooled on ice to deactivate the M-MLV RTase. 1 μl of the cDNA synthesized by the method was mixed with 10× buffer ($MgCl_2$ free), 2.5 mM dNTPs, 10×$MgCl_2$, and Taq DNA polymerase. 10 pmol of primer for TSPYL5 or β-actin was added to the mixture and amplified under the following conditions. Then, for TSPYL5 primer, EcoRI/Forward: 5'-CCG-GAATTCATGAGCGGCCGAAGTCGGGGT-3' (SEQ ID NO:3) as a forward primer and EcoRI/reverse: 5'-CCG-GAATTCTC AGTTGGATTGGCTCACCCC-3' (SEQ ID NO:4) as a reverse primer were used. Pre-denaturation at 94° C. for 5 min, denaturation at 94° C. for 1 min, annealing at 60° C. for 1.5 min, 45 cycles of elongation at 72° C. for 1 min were performed, followed by post-elongation at 72° C. for 10 min. After the PCR, the expression level of the TSPYL5 gene was identified by electrophoresis on 1% agarose gel.

Figure 2:
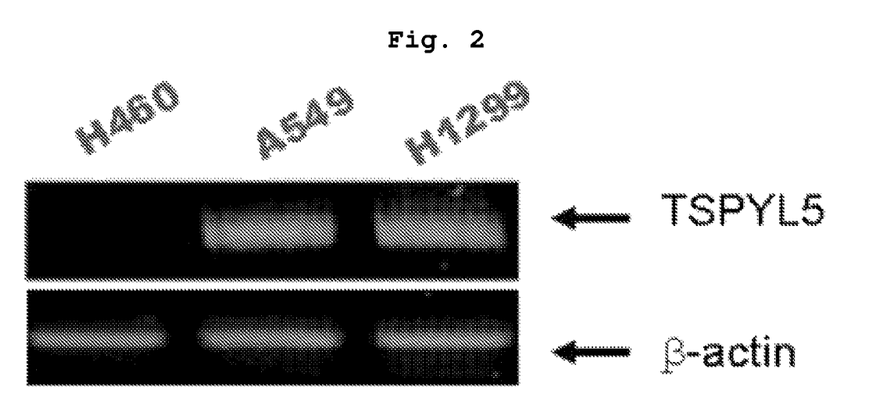
FIG. 2 is a photo illustrating a measurement of the expression level of TSPYL5 in lung cancer cell lines A549, H460, and H1299 by RT-PCR.

As illustrated in FIG. 2, the results show that the expression level of the TSPYL5 gene in A549 and H1299 cell lines with resistance to radiation and anticancer agents were significantly increased, compared to that in H460 cell line (FIG. 2).

Example 2

Quantitative Analysis of TSPYL5 Methylation Using Pyrosequencing

In order to confirm the methylation status of CpG islands in the promoter region present in TSPYL5, pyrosequencing was performed on each promoter of the TSPYL5 gene in lung cancer cell lines H460, A549, and H1299. In order to convert unmethylated cytosine to uracil by using bisulfite, total genomic DNA was isolated from each of H460, A549, and H1299 and the bisulfite was treated by using an EZ DNA methylation-Gold kit (Zymo Research, USA) to 200 ng of the genomic DNA. If DNA was treated with bisulfite, unmethylated cytosine was converted to uracil, while methylated cytosine was maintained without modification. Pyrosequencing was performed by eluting the bisulfite-treated DNA with 20 μl of sterile distilled water. 20 ng of bisulfite-treated genomic DNA was amplified by PCR. For PCR primer, a forward primer: 5'-TTAGAAAATAGGTGATGGGGATA-3' (SEQ ID NO:5) and a reverse primer: 5'-Biotin-AAATAC-TACCATTTCATCTCTTCC-3' (SEQ ID NO:6) were used. PCR was performed with denaturation at 95° C. for 5 min, followed by 45 cycles of treatment at 95° C. for 45 sec, at 62° C. for 45 sec, at 72° C. for 30 sec, with a final elongation at 72° C. for 5 min. Next, the biotin-marked template DNA was purified, followed by sequencing reaction with PyroMark ID (Biotage, USA). 5'-GGTGGTGATGGTTTTTA-3' (SEQ ID NO:7) was used as a sequencing primer, and the PCR and sequencing primers were designed using PSQ assay design program (Biotage, USA). The underlined base sequence in the following [Table 1] indicates a pyrosequencing region of TSPYL5.

TABLE 1

| TSPYL5<br>(−280~−161nt,<br>y: CpG site)<br>(SEQ ID No: 14) | GTTTAGTTTA GAAAATAGGT GATGGGGGAT<br>AGGTGGTGAT GGTTTTTAGY GTTGTTTTGT<br>TTAAYGAGAT TTTGAGAGTA YGATGAGTTY<br>GYGYGGAAGA GATGAAATGG TAGTATT |
|---|---|
| TSPYL5 sequencing primer: | 5'-GGTGGTGAT GGTTTTTA-3'<br>(SEQ ID No: 7) |
| TSPYL5 sequence to analyze: | GYGTTGTTTTGTTTAAYGAGATTTTGAGAGTA<br>YGATGAGTTYGYGYGGA<br>(SEQ ID No: 15) |

Y: methylated position in H460 and/or A549 (position 1 to 6).

Figure 3:
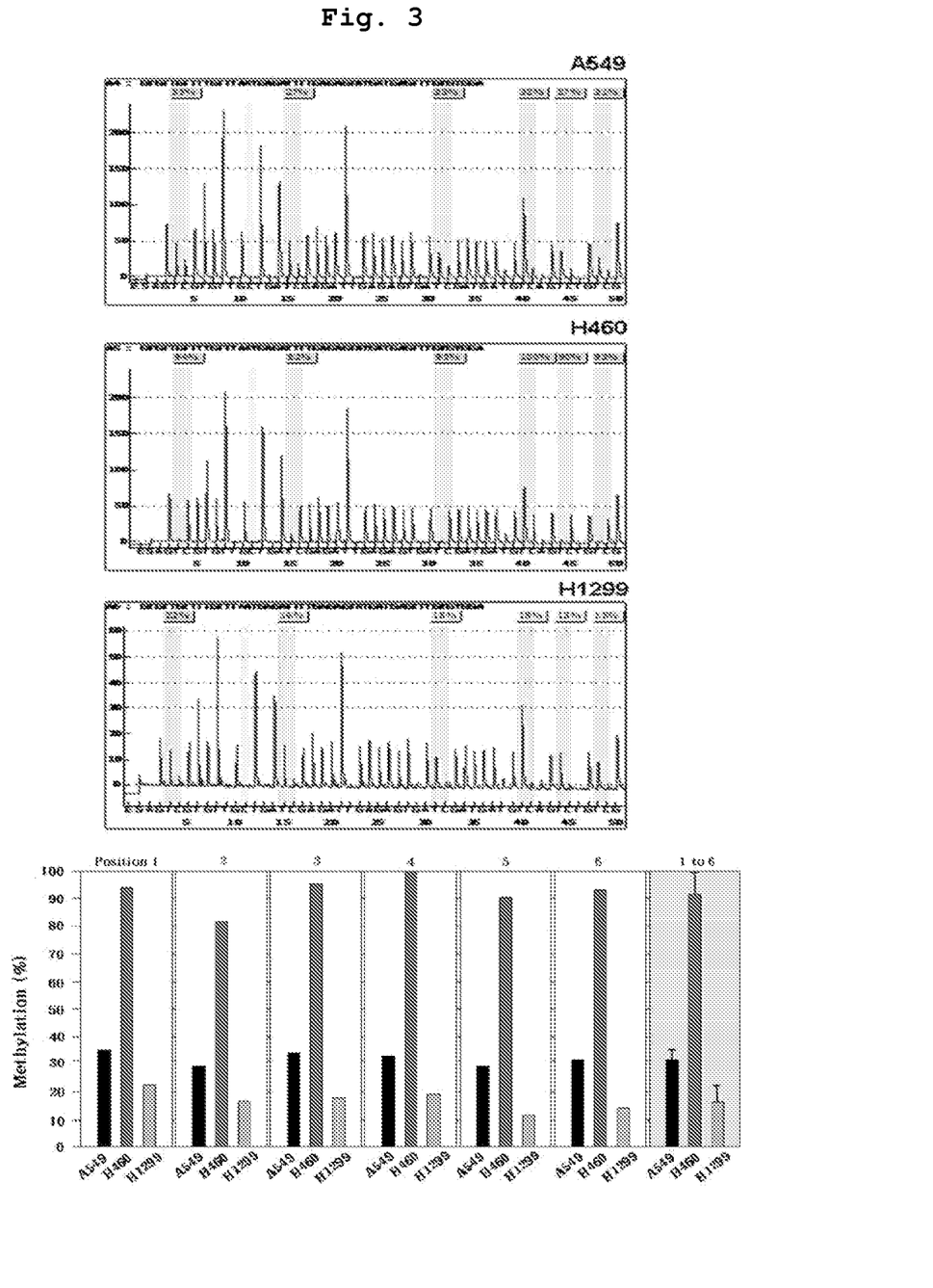
FIG. 3 is a group of graphs illustrating the results of quantitative analysis (top) and the results of quantitative analysis with an error value in the form of a longitudinal bar graph (bottom), of TSPYL5 methylation in lung cancer cell lines A549, H460, and H1299 by using pyrosequencing.

As illustrated in FIG. 3, the results show that more methylation in H460 cell line was achieved than those in A549 and H1299 cell lines by about 3 times and about 4.5 times, respectively (FIG. 3).

Example 3

Inhibition of Expression of TSPYL5 Gene in Lung Cancer Cell Lines by Using siRNA <3-1> Preparation and Transduction of TSPYL5-siRNA Duplex Oligoribonucleotides The genetic sequence information of the siRNA for the TSPYL5 gene was submitted to Invitrogen Corp, and then 3 kinds of 25mer TSPYL5 stealth-RNAi prepared by custom service, described in the following Table 2 were used. Introduction of the siRNA into the cell was performed by using Lipofectamine RNAi MAX (Invitrogen) with 40~80 nM of each RNAi from $2 \times 10^5$ cells of A549 and H1299 cells. TSPYL5-siRNA duplex oligoribonucleotides were transduced into cells in an antibiotic (penicillin-streptomycin solution (Hyclone))-free medium, subjected to reaction for 4 to 6 hours, and then incubated in a medium supplemented with 100 units/Ml of penicillin-streptomycin solution.

TABLE 2

| | Primer sequence (5'-3') |
|---|---|
| HSS131713<br>(C1) | (RNA)-ACCACACCCAUAUUCCUUGAUGAGC<br>(SEQ ID No: 8) |
| HSS131713'<br>(C1) | (RNA)-GCUCAUCAAGGAAUAUGGGUGUGGU<br>(SEQ ID No: 9) |
| HSS131714<br>(C2) | (RNA)-AAAGGUAGAACUGCAAGGGAUUGGG<br>(SEQ ID No: 10) |
| HSS131714'<br>(C2) | (RNA)-CCCAAUCCCUUGCAGUUCUACCUUU<br>(SEQ ID No: 11) |
| HSS131715<br>(C3) | (RNA)-UUCUUCUGCCUCCCACCAGCUAUGA<br>(SEQ ID No: 12) |
| HSS131715'<br>(C3) | (RNA)-UCAUAGCUGGUGGGAGGCAGAAGAA<br>(SEQ ID No: 13) |

<3-2> Incubation of Lung Cancer Cells Transduced

Cells (negative control; siControl) transduced with Scrambled Stealth™ RNA molecule and cells transduced with siRNA duplex oligoribonucleotides inhibiting the expression of TSPYL5, in human lung cancer cell lines A549 and H1299, were incubated at $1 \times 10^5$ cells/Ml in a RPMI medium supplemented with 100 units/Ml of penicillin-streptomycin solution (Hyclone) and 10% bovine fetal serum (Hyclone) at 37° C. in a 5% $CO_2$ incubator.

<3-3> Confirmation of the Expression Level of TSPYL5 Gene in Lung Cancer Cell Lines Transduced with siRNA by Reverse Transcription Polymerase Chain Reaction (RT-PCR)

According to a RT-PCR method in the Example <1-2>, the expression levels of cells (negative control; siControl) transduced with Scrambled Stealth™ RNA molecule and cells (C1-131713, C2-131714, and C3-131715) transduced with 3 kinds of TSPYL5-siRNA duplex oligoribonucleotides as candidate primers, in human lung cancer cell lines A549 and H1299, were confirmed.

As illustrated in FIG. 4, the results show that the expression levels of TSPYL5 in cells transduced with TSPYL5-siRNA were reduced compared to the expression levels in cells (negative control; siControl) transduced with Scrambled Stealth™ RNA molecule, and the expression levels of TSPYL5 in C2-131714 among the 3 kinds of TSPYL5-siRNA (25mers) had been reduced the most effectively in A549 and H1299 cell lines (FIG. 4).

Example 4

Analysis of Effects of Inhibition of Expression of TSPYL5 on Sensitivity of Cells to Cisplatin In order to observe the sensitivity to anticancer agents in a lung cancer cell line in which the expression of TSPYL5 had been inhibited, flowcytometry was performed. After 72 hours from transduction of TSPYL5-siRNA according to the <Example 3>, incubated cells ($5 \times 10^5$) were obtained, suspended in 500 μl of 70% iced ethanol, fixed at −20° C. for 30 min, centrifuged to remove the ethanol, followed by phosphate buffered saline (PBS) washing. Next, the cells were treated with cisplatin (Plantinol AQ, USA) at 100 or 200 μM for 24 hours, suspended in 500 μl of propidium iodide (PI) staining reagent (PBS, pH 7.4, 0.1% Triton X-100, 0.1 mM EDTA, 0.05 mg/Ml RNase A (50 units/mg), 50 μg/Ml PI) at 4° C. for 1 hour for staining, followed by flow cytometry to analyze apoptosis and cell cycle of the cells.

Figure 5:
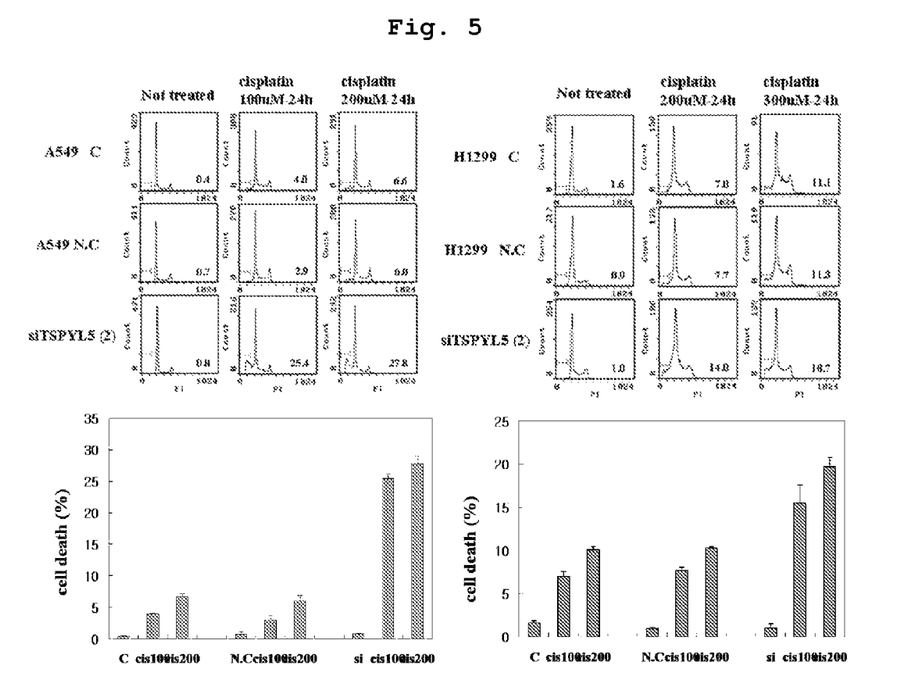
FIG. 5 is a group of graphs illustrating the effects of inhibition of the expression of TSPYL5 on sensitivity of cells to cisplatin by flowcytometry (top) and the results of flowcytometry with an error value in the form of a longitudinal bar graph (bottom).

As illustrated in FIG. 5, the results show that apoptosis was increased in a cell line transduced with TSPYL5-siRNA than that in a control group and negative control group of the 549 cell line and that in the H1299 cell line by about 5 times and about 2 times, respectively. In other words, it was confirmed that the inhibition of expression of TSPYL5 effectively induced apoptosis by cisplatin in a lung cancer cell (FIG. 5).

Example 5

Analysis of Effects of Inhibition of the Expression of TSPYL5 on Sensitivity of Cells after Gamma-Radiation Treatment <5-1> Confirmation of Sensitivity of Cells by Flowcytometry In order to observe the sensitivity to radiation in a lung cancer cell line in which the expression of TSPYL5 had been inhibited, flowcytometry was performed by using a gamma-ray irradiation facility (source; $^{60}C_0$) in Korea Atomic Energy Research Institute (KAERI) to irradiate gamma-ray. After 48 hours from transduction of TSPYL5-siRNA according to the <Example 3>, cells were irradiated with 10 Gy. Incubated cells (5×10⁵) were obtained, suspended in 500 μl of 70% iced ethanol, fixed at −20° C. for 1 hour, centrifuged to remove the ethanol, washed with phosphate buffered saline (PBS), followed by staining with 500 μl of PI staining reagent at 37° C. for 1 hour. Subsequently, apoptosis and cell cycle was analyzed by flowcytometry.

Figure 6:
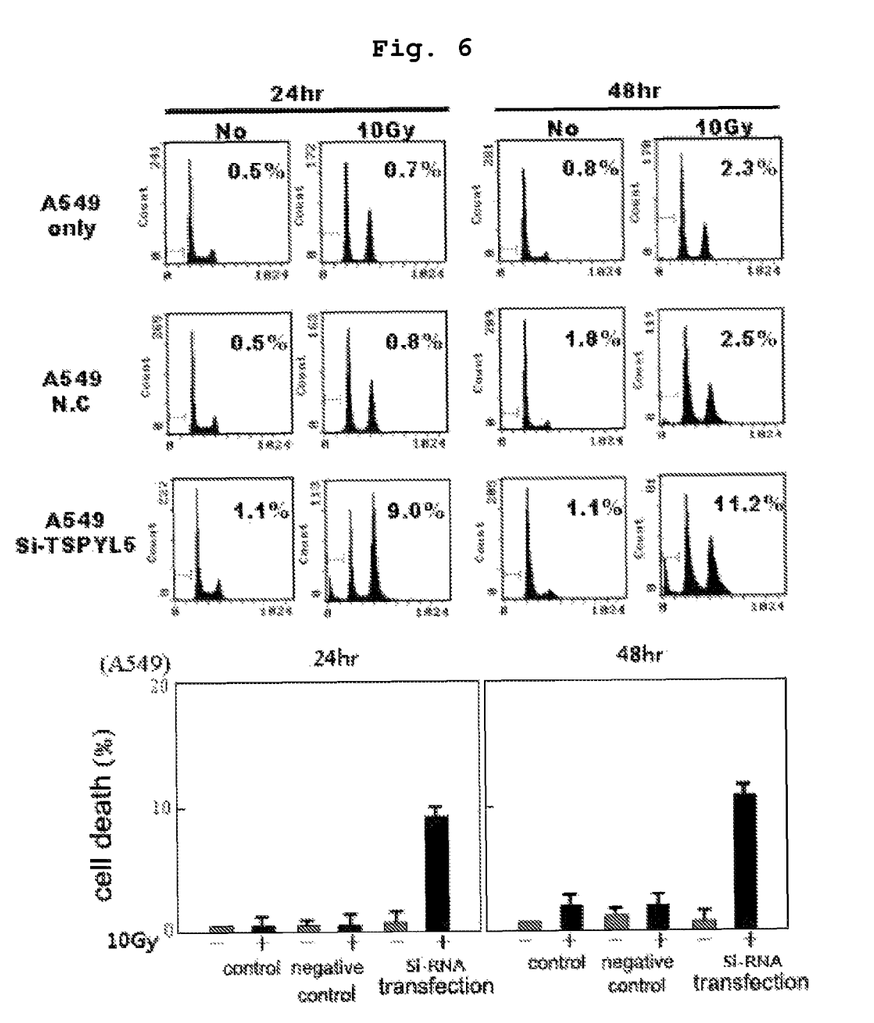
FIG. 6 is a group of graphs illustrating the effects of inhibition of the expression of TSPYL5 after being subjected to gamma-radiation on sensitivity of cells to gamma-radiation over time by flowcytometry (top) and the results of flowcytometry with an error value in the form of a longitudinal bar graph (bottom).

As illustrated in FIG. 6, it was confirmed that inhibition of the expression of TSPYL5 effectively induced apoptosis by irradiation of radiation (FIG. 6).

<5-2> Confirmation of Sensitivity of Cells by Colony Forming Assay

In order to observe the sensitivity to radiation in a lung cancer cell line in which the expression of TSPYL5 had been inhibited, colony formation assay was performed by using a gamma-ray irradiation facility (source;$^{60}C_0$) in Korea Atomic Energy Research Institute (KAERI) to irradiate gamma-ray. A549 cell line was inoculated at a density of 2×10³ cells/35-mm dish, and siRNA prepared by custom service at 5 or 10 nM in the Table 1 and negative control group at 10 nM were transduced into the A549 cell line in a bovine fetal serum-free medium by Lipofectamine RNAi MAX (Invitrogen). After 6 hours from the transduction, incubation was performed in a medium supplemented with bovine fetal serum. After 48 hours from the transduction, cells were irradiated with 10 Gy and incubated in a 5% $CO_2$ incubator for 5 to 10 days. After 10 days of incubation, colony was washed twice with PBS, stained with crystal violet solution for 10 min, and washed 5 times with PBS to observe the colony.

Figure 7:
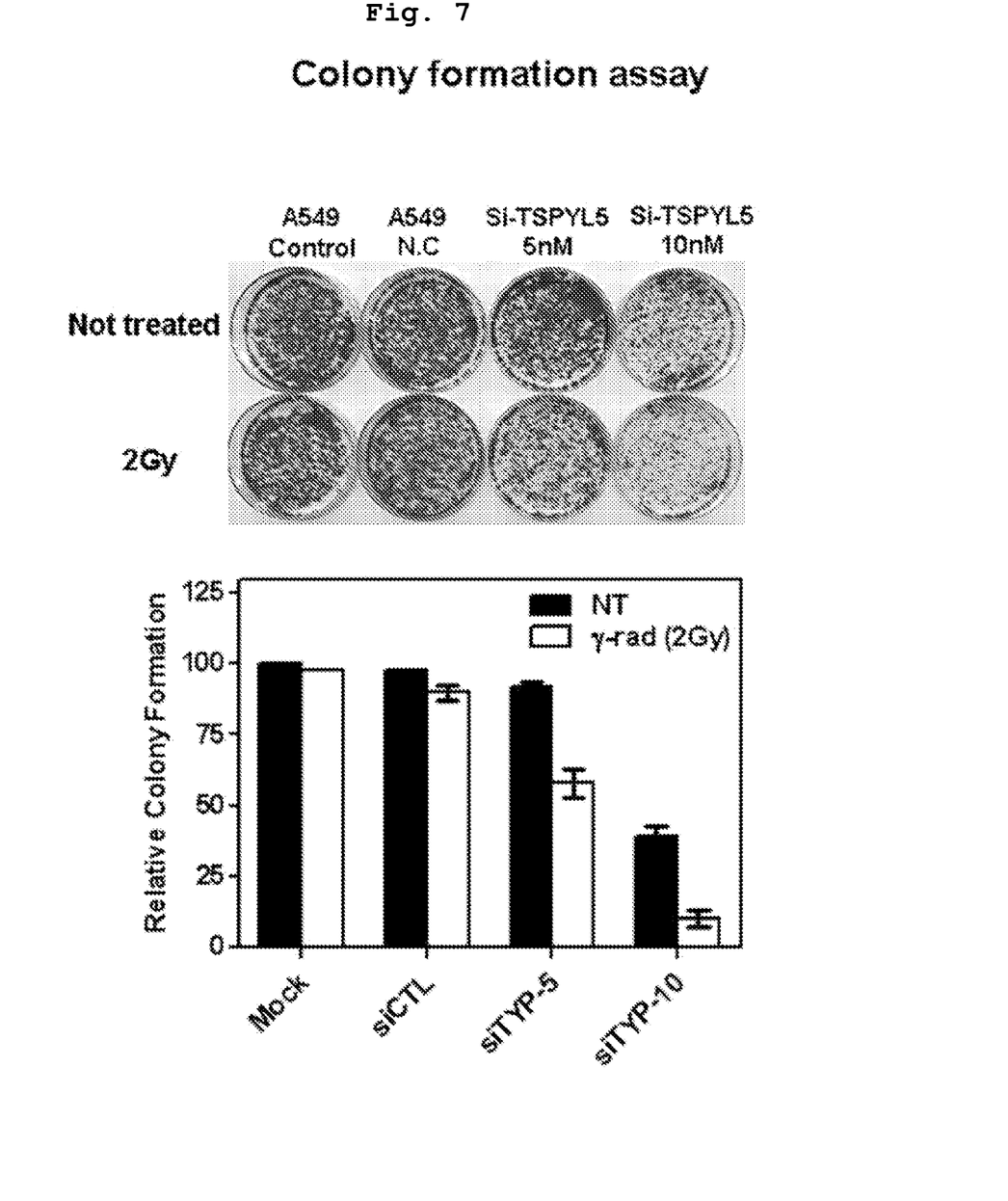
FIG. 7 is a graph illustrating the effects of inhibition of the expression of TSPYL5 on sensitivity of cells to gamma-radiation by colony forming assay.

As illustrated in FIG. 7, the results show that no differences in colony formation were observed in control groups and cell lines transduced with negative control group when gamma-radiation of 2 Gy was irradiated in the A549 cell line. However, in the case of a cell line transduced with TSPYL5-siRNA, colony formation was reduced by concentration of siRNA and significantly reduced due to synergistic effects from the gamma-ray irradiation (FIG. 7).

Example 6

Analysis of Effects of Inhibition of the Expression of TSPYL5 on the Expression of Protein In order to analyze the expression of protein in a lung cancer, a specific protein expression assay (Western blot) was performed. The A549 cell line was inoculated at a density of 1×10⁵ cells per well in a 6-well petri dish, and siRNA prepared by custom service at 100 nM in the Table 2 and negative control group at 100 nM were transduced into the A549 cell line in a bovine fetal serum-free medium by Lipofectamine RNAi MAX (Invitrogen). After 6 hours from the transduction, incubation was performed in a medium supplemented with bovine fetal serum. After 48 hours from the transduction, cells were collected, cell lysis solution (RIPA lysis buffer-santa cruz, USA) was used to extract protein, and 40 μg of protein was assayed with Bradford assay kit (total protein kit, sigma) to confirm the expression of the protein. Bovine serum albumin (BSA, Amesco) was used to remove antibodies non-specifically binding to the surface of protein. Selective protein antibodies in the following Table 3 were diluted for binding to protein, and color developing enzymes from identification of these antibodies were again bound to the antibodies for analysis of their exposure to film.

TABLE 3

| Selective protein antibodies | Dilution ratio | Antibody recognition enzymes | Dilution ratio |
|---|---|---|---|
| a-bax (upstate, USA) | 1:1000 | a-rabbit (cell signaling, USA) | 1:1000 |
| a-pAKT (cell signaling, USA) | 1:500 | | |
| a-bcl2 (santa cruz, USA) | | a-mouse (cell signaling, USA) | |
| a-p53 (santa cruz, USA) | | | |
| a-pTEN (santa cruz, USA) | | | |
| a-p21 (santa cruz, USA) | | | |

Figure 8:
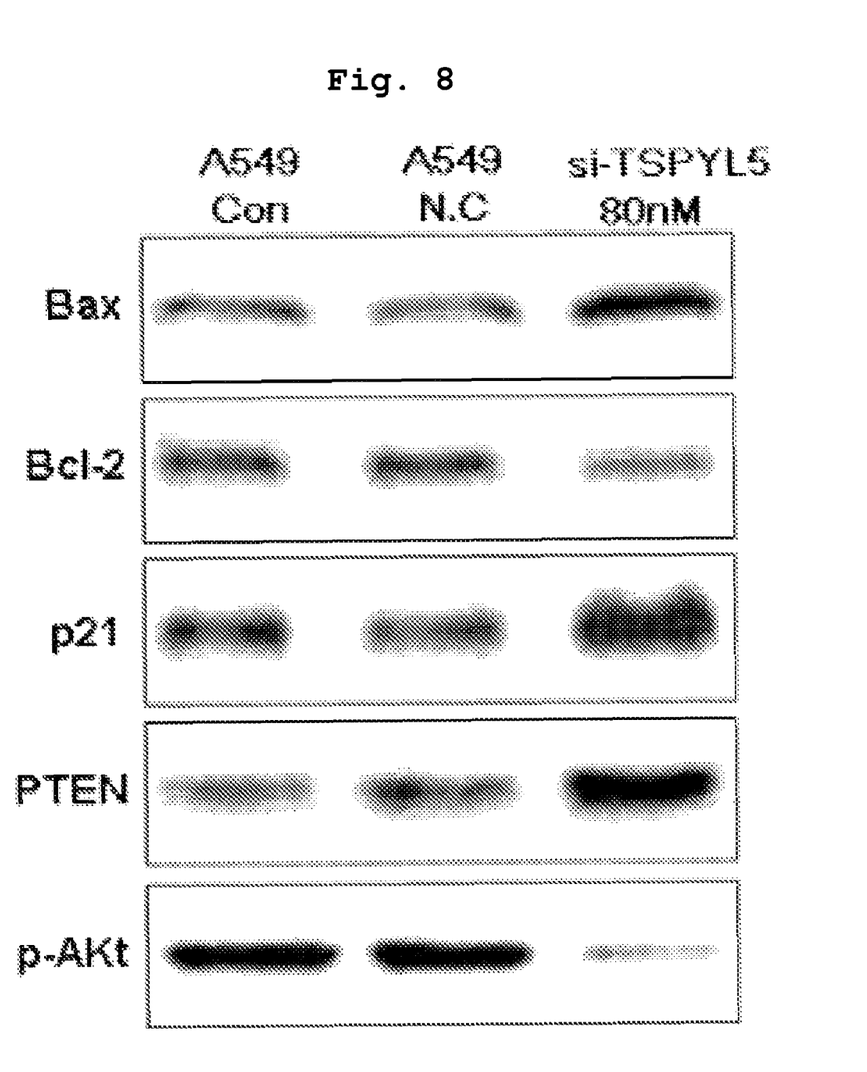
FIG. 8 is a group of photos confirming the effects of inhibition of the expression of TSPYL5 on the expression of proteins by a specific protein expression assay (Western blot).

As a result, as illustrated in FIG. 8, when the A549 cell line was transduced with TSPYL5-siRNA, the expression of a-bax protein associated with apoptosis was increased and the expression of a-bcl2 protein associated with anti-apoptosis was inhibited. It was also confirmed that the expressions of the carcinogenesis suppressor gene a-pTEN and the cell proliferation regulatory factor a-p21 were increased and the expression of the cell survival promoting gene a-pAKT was decreased (FIG. 8).

Because apoptosis may be maximized by inhibiting the expression of the testis-specific protein, Y-encoded-like 5 (TSPYL5) gene of the present invention to enhance the sensitivity of cancer cells to stress such as radiation or anticancer agents, the method of the present invention may be very usefully used for anticancer treatment when used in combination with radiotherapy or chemotherapy.

As described above, because inhibitors of expression or activity of testis-specific protein, Y-encoded-like 5 (TSPYL5) enhance the sensitivity of lung cancer cell line to anticancer agents and radiation to promote the apoptosis of the cell line, they may be usefully used for research and development of anticancer agents or anticancer supplement agents for prevention and treatment of cancer due to increase in expression or activity of TSPYL5, and usefully used for development and production of new anticancer candidate materials by screening the candidate materials using inhibitors of expression or activity of TSPYL5.

Any sequence listing, including such submitted as an electronic ASCII text file, is expressly incorporated by reference and considered part of the specification herewith.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for enhancing sensitivity of lung cancer cells to cisplatins or gamma-radiation, comprising: administering to lung cancer cells having resistance to cisplatins and gamma-radiation an anticancer supplement agent comprising an inhibitor of the expression of testis protein, Y-encoded-like 5 (TSPYL5) protein, wherein said TSPYL5 protein has an amino acid sequence of SEQ ID No: 1, wherein the inhibitor of the expression of the TSPYL5 protein is an antisense oligonucleotide or nucleic acid that is complementary to TSPYL5 mRNA and can bind to the mRNA thereby inhibiting expression of the mRNA, or a small interfering RNA (siRNA) that is complementary to TSPYL5 mRNA and can bind to the mRNA thereby inhibiting expression of the mRNA.

* * * * *

SEQUENCE LISTING

<160> NUMBER OF SEQ ID NOS: 15

<210> SEQ ID NO 1
<211> LENGTH: 417
<212> TYPE: PRT

-continued

<213> ORGANISM: Homo sapiens

<400> SEQUENCE: 1

```
Met Ser Gly Arg Ser Arg Gly Arg Lys Ser Arg Ala Lys Asn Arg
 1               5                  10                  15

Gly Lys Gly Arg Ala Lys Ala Arg Val Arg Pro Ala Pro Asp Asp Ala
                20                  25                  30

Pro Arg Asp Pro Asp Pro Ser Gln Tyr Gln Ser Leu Gly Glu Asp Thr
            35                  40                  45

Gln Ala Ala Gln Val Gln Ala Gly Ala Trp Gly Gly Leu Glu Ala
     50                  55                  60

Ala Ala Ser Ala Gln Leu Leu Arg Leu Gly Glu Ala Ala Cys Arg
 65                  70                  75                  80

Leu Pro Leu Asp Cys Gly Leu Ala Leu Arg Ala Arg Ala Gly Asp
                 85                  90                  95

His Gly Gln Ala Ala Arg Pro Gly Pro Gly Lys Ala Ala Ser Leu
                100                 105                 110

Ser Glu Arg Leu Ala Ala Asp Thr Val Phe Val Gly Thr Ala Gly Thr
                115                 120                 125

Val Gly Arg Pro Lys Asn Ala Pro Arg Val Gly Asn Arg Arg Gly Pro
            130                 135                 140

Ala Gly Lys Lys Ala Pro Glu Thr Cys Ser Thr Ala Gly Arg Gly Pro
145                 150                 155                 160

Gln Val Ile Ala Gly Gly Arg Gln Lys Lys Gly Ala Ala Gly Glu Asn
                165                 170                 175

Thr Ser Val Ser Ala Gly Glu Glu Lys Lys Glu Arg Asp Ala Gly
                180                 185                 190

Ser Gly Pro Pro Ala Thr Glu Gly Ser Met Asp Thr Leu Glu Asn Val
            195                 200                 205

Gln Leu Lys Leu Glu Asn Met Asn Ala Gln Ala Asp Arg Ala Tyr Leu
    210                 215                 220

Arg Leu Ser Arg Lys Phe Gly Gln Leu Arg Leu Gln His Leu Glu Arg
225                 230                 235                 240

Arg Asn His Leu Ile Gln Asn Ile Pro Gly Phe Trp Gly Gln Ala Phe
                245                 250                 255

Gln Asn His Pro Gln Leu Ala Ser Phe Leu Asn Ser Gln Glu Lys Glu
                260                 265                 270

Val Leu Ser Tyr Leu Asn Ser Leu Glu Val Glu Glu Leu Gly Leu Ala
            275                 280                 285

Arg Leu Gly Tyr Lys Ile Lys Phe Tyr Phe Asp Arg Asn Pro Tyr Phe
290                 295                 300

Gln Asn Lys Val Leu Ile Lys Glu Tyr Gly Cys Gly Pro Ser Gly Gln
305                 310                 315                 320

Val Val Ser Arg Ser Thr Pro Ile Gln Trp Leu Pro Gly His Asp Leu
                325                 330                 335

Gln Ser Leu Ser Gln Gly Asn Pro Glu Asn Asn Arg Ser Phe Phe Gly
            340                 345                 350

Trp Phe Ser Asn His Ser Ser Ile Glu Ser Asp Lys Ile Val Glu Ile
            355                 360                 365

Ile Asn Glu Glu Leu Trp Pro Asn Pro Leu Gln Phe Tyr Leu Leu Ser
    370                 375                 380

Glu Gly Ala Arg Val Glu Lys Gly Lys Glu Lys Glu Gly Arg Gln Gly
385                 390                 395                 400

Pro Gly Lys Gln Pro Met Glu Thr Thr Gln Pro Gly Val Ser Gln Ser
```

Asn

<210> SEQ ID NO 2
<211> LENGTH: 1254
<212> TYPE: DNA
<213> ORGANISM: Homo sapiens

<400> SEQUENCE: 2

```
atgagcggcc gaagtcgggg tcgaaagtcc tcccgcgcca aaaaccgggg caaaggccgc      60
gccaaagccc gagtccgccc tgctccggac gacgccccgc gcgacccgga cccttcacag     120
taccagagtc tcgggaaga cacccaggcg gcacaggtgc aggctggcgc ggggtggggt     180
ggcctggaag ccgctgcgtc cgcgcagctc ctccggctcg ggaggaggc cgcctgccgg     240
ctcccctgg actgtggcct cgcgctgcgg gcccgagctg cggggacca cgggcaggcc     300
gcggccaggc ccgcccggg gaaggccgca tctctctcgg agcgcctggc cgcagacact     360
gtcttcgtgg aacagcggg aaccgtggga aggccgaaaa atgcccccg cgttggaaac     420
cggcgtggcc ctgccgggaa gaaggcccca gaaacctgta gcaccgcggg gaggggcct     480
caggtcatag ctggtgggag gcagaagaaa ggggcggcag gggagaatac ctcggtgtca     540
gctggggagg aaaagaagga agagagggat gcagggtcgg ggcccccagc gacggaaggc     600
agcatggata cgctggagaa cgtgcagctg aagctggaga acatgaacgc ccaggcggac     660
agggcctacc ttcggctctc caggaagttt gggcagttgc gactgcagca cttggagcgc     720
aggaaccacc tcatccaaaa tatcccgggc ttctggggc aagcatttca gaaccatccc     780
cagctagcat cctttctgaa tagccaagag aaagaggtac tgagctactt aaacagcttg     840
gaagtggaag agctcggcct tgccagattg ggctacaaaa tcaagttcta cttcgatcgc     900
aacccgtatt ccaaaataa ggtgctcatc aaggaatatg ggtgtggtcc ttctggccag     960
gtggtgtctc gttctactcc aatccagtgg ctcccagggc atgatctcca gtccctaagc    1020
cagggaaacc cagaaacaa ccgtagtttc tttgggtggt tttcaaacca cagctccatt    1080
gagtctgaca agattgtgga gataatcaac gaagaattgt ggcccaatcc cttgcagttc    1140
tacctttga gtgaaggggc tcgtgtagag aaaggaaagg aaaaagaagg caggcaaggt    1200
ccaggaaagc agccaatgga gactactcag cctggggtga gccaatccaa ctga          1254
```

<210> SEQ ID NO 3
<211> LENGTH: 30
<212> TYPE: DNA
<213> ORGANISM: Artificial Sequence
<220> FEATURE:
<223> OTHER INFORMATION: TSPYL5 EcoR1/forward primer

<400> SEQUENCE: 3

```
ccggaattca tgagcggccg aagtcggggt                                       30
```

<210> SEQ ID NO 4
<211> LENGTH: 30
<212> TYPE: DNA
<213> ORGANISM: Artificial Sequence
<220> FEATURE:
<223> OTHER INFORMATION: TSPYL5 EcoR1/reverse primer

<400> SEQUENCE: 4

```
ccggaattct cagttggatt ggctcacccc                                       30
```

<210> SEQ ID NO 5

```
<211> LENGTH: 24
<212> TYPE: DNA
<213> ORGANISM: Artificial Sequence
<220> FEATURE:
<223> OTHER INFORMATION: TSPYL5 forward primer

<400> SEQUENCE: 5
ttagaaaata ggtgatgggg gata                                              24

<210> SEQ ID NO 6
<211> LENGTH: 24
<212> TYPE: DNA
<213> ORGANISM: Artificial Sequence
<220> FEATURE:
<223> OTHER INFORMATION: TSPYL5 reverse primer

<400> SEQUENCE: 6
aaatactacc atttcatctc ttcc                                              24

<210> SEQ ID NO 7
<211> LENGTH: 17
<212> TYPE: DNA
<213> ORGANISM: Artificial Sequence
<220> FEATURE:
<223> OTHER INFORMATION: TSPYL5 sequencing primer

<400> SEQUENCE: 7
ggtggtgatg gttttta                                                      17

<210> SEQ ID NO 8
<211> LENGTH: 25
<212> TYPE: RNA
<213> ORGANISM: Artificial Sequence
<220> FEATURE:
<223> OTHER INFORMATION: TSPYL5 stealth-RNAi

<400> SEQUENCE: 8
accacaccca uauccuuga ugagc                                              25

<210> SEQ ID NO 9
<211> LENGTH: 25
<212> TYPE: RNA
<213> ORGANISM: Artificial Sequence
<220> FEATURE:
<223> OTHER INFORMATION: TSPYL5 stealth-RNAi

<400> SEQUENCE: 9
gcucaucaag gaauaugggu guggu                                             25

<210> SEQ ID NO 10
<211> LENGTH: 25
<212> TYPE: RNA
<213> ORGANISM: Artificial Sequence
<220> FEATURE:
<223> OTHER INFORMATION: TSPYL5 stealth-RNAi

<400> SEQUENCE: 10
aaagguagaa cugcaaggga uuggg                                             25

<210> SEQ ID NO 11
<211> LENGTH: 25
<212> TYPE: RNA
<213> ORGANISM: Artificial Sequence
<220> FEATURE:
<223> OTHER INFORMATION: TSPYL5 stealth-RNAi

<400> SEQUENCE: 11
```
cccaaucccu ugcaguucua ccuuu                                          25

<210> SEQ ID NO 12
<211> LENGTH: 25
<212> TYPE: RNA
<213> ORGANISM: Artificial Sequence
<220> FEATURE:
<223> OTHER INFORMATION: TSPYL5 stealth-RNAi

<400> SEQUENCE: 12
uucuucugcc ucccaccagc uauga                                          25

<210> SEQ ID NO 13
<211> LENGTH: 25
<212> TYPE: RNA
<213> ORGANISM: Artificial Sequence
<220> FEATURE:
<223> OTHER INFORMATION: TSPYL5 stealth-RNAi

<400> SEQUENCE: 13
ucauagcugg ugggaggcag aagaa                                          25

<210> SEQ ID NO 14
<211> LENGTH: 117
<212> TYPE: DNA
<213> ORGANISM: Artificial Sequence
<220> FEATURE:
<223> OTHER INFORMATION: TSPYL5 (-280~-161nt, y: CpG site)
<220> FEATURE:
<221> NAME/KEY: variation
<222> LOCATION: (50)..(50)
<223> OTHER INFORMATION: n is methylated position in H460 and/or A549
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: variation
<222> LOCATION: (65)..(65)
<223> OTHER INFORMATION: n is methylated position in H460 and/or A549
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: variation
<222> LOCATION: (81)..(81)
<223> OTHER INFORMATION: n is methylated position in H460 and/or A549
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: variation
<222> LOCATION: (90)..(90)
<223> OTHER INFORMATION: n is methylated position in H460 and/or A549
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: variation
<222> LOCATION: (92)..(92)
<223> OTHER INFORMATION: n is methylated position in H460 and/or A549
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: variation
<222> LOCATION: (94)..(94)
<223> OTHER INFORMATION: n is methylated position in H460 and/or A549
<220> FEATURE:
<221> NAME/KEY: misc_feature
<222> LOCATION: (94)..(94)

```
<223> OTHER INFORMATION: n is a, c, g, or t

<400> SEQUENCE: 14
gtttagttta gaaaataggt gatgggggat aggtggtgat ggtttttagn gttgttttgt      60
ttaangagat tttgagagta ngatgagttn gngnggaaga gatgaaatgg tagtatt        117

<210> SEQ ID NO 15
<211> LENGTH: 49
<212> TYPE: DNA
<213> ORGANISM: Artificial Sequence
<220> FEATURE:
<223> OTHER INFORMATION: TSPYL5 sequence to analyze
<220> FEATURE:
<221> NAME/KEY: variation
<222> LOCATION: (2)..(2)
<223> OTHER INFORMATION: n is methylated position in H460 and/or A549
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: variation
<222> LOCATION: (17)..(17)
<223> OTHER INFORMATION: n is methylated position in H460 and/or A549
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: variation
<222> LOCATION: (33)..(33)
<223> OTHER INFORMATION: n is methylated position in H460 and/or A549
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: variation
<222> LOCATION: (42)..(42)
<223> OTHER INFORMATION: n is methylated position in H460 and/or A549
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: variation
<222> LOCATION: (44)..(44)
<223> OTHER INFORMATION: n is methylated position in H460 and/or A549
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: variation
<222> LOCATION: (46)..(46)
<223> OTHER INFORMATION: n is methylated position in H460 and/or A549
<220> FEATURE:
<221> NAME/KEY: misc_feature
<222> LOCATION: (46)..(46)
<223> OTHER INFORMATION: n is a, c, g, or t

<400> SEQUENCE: 15
gngttgtttt gtttaangag attttgagag tangatgagt tngngngga                  49
```